US 9,089,872 B2

(12) United States Patent
Nakamura et al.

(10) Patent No.: US 9,089,872 B2
(45) Date of Patent: Jul. 28, 2015

(54) ULTRASONIC TRANSDUCER ELEMENT CHIP, PROBE, ELECTRONIC INSTRUMENT, AND ULTRASONIC DIAGNOSTIC DEVICE

(71) Applicant: SEIKO EPSON CORPORATION, Tokyo (JP)

(72) Inventors: Tomoaki Nakamura, Nagano (JP); Jiro Tsuruno, Nagano (JP); Kanechika Kiyose, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 330 days.

(21) Appl. No.: 13/804,689

(22) Filed: Mar. 14, 2013

(65) Prior Publication Data

US 2013/0258802 A1    Oct. 3, 2013

(30) Foreign Application Priority Data

Mar. 30, 2012 (JP) ................. 2012-078673

(51) Int. Cl.
| | | |
|---|---|---|
| B06B 1/02 | (2006.01) | |
| G01S 7/56 | (2006.01) | |
| H04R 1/20 | (2006.01) | |
| H04R 31/00 | (2006.01) | |
| G01S 15/89 | (2006.01) | |
| G01S 7/52 | (2006.01) | |
| B06B 1/06 | (2006.01) | |

(52) U.S. Cl.
CPC .............. *B06B 1/0207* (2013.01); *B06B 1/0622* (2013.01); *G01S 7/5208* (2013.01); *G01S 7/56* (2013.01); *G01S 15/8925* (2013.01); *H04R 1/20* (2013.01); *H04R 31/00* (2013.01); *Y10T 29/49005* (2015.01)

(58) Field of Classification Search
CPC ....... B06B 1/0207; B06B 1/0622; G01S 7/56; G01S 7/5208; G01S 15/8925; H04R 1/20; H04R 31/00; Y10T 29/49005; G03B 42/06
USPC .......................................... 367/140
See application file for complete search history.

(56) References Cited

U.S. PATENT DOCUMENTS

| | | | |
|---|---|---|---|
| 7,622,849 | B2 | 11/2009 | Watanabe et al. |
| 8,169,855 | B2 | 5/2012 | Nakamura |

(Continued)

FOREIGN PATENT DOCUMENTS

| | | |
|---|---|---|
| JP | 02-114947 A | 4/1990 |
| JP | 2010-183437 A | 8/2010 |

(Continued)

*Primary Examiner* — Daniel Pihulic
(74) *Attorney, Agent, or Firm* — Global IP Counselors, LLP

(57) ABSTRACT

An ultrasonic transducer element chip includes a substrate, ultrasonic transducer elements and a reinforcing member. The substrate defines openings arranged in an array pattern. The ultrasonic transducer elements are respectively disposed at the openings on a first surface of the substrate. The reinforcing member is fixed on a second surface of the substrate opposite to the first surface of the substrate. The reinforcing member includes linear groove parts formed on a surface of the reinforcing member fixed on the substrate so that internal spaces of the openings and an external space of the substrate are in communication with each other via the linear groove parts. The linear groove parts extend along a plane of the surface of the reinforcing member, and they are arranged at an interval in a first direction smaller than a width of each opening on the second surface of the substrate in the first direction.

13 Claims, 11 Drawing Sheets

(56) References Cited

U.S. PATENT DOCUMENTS

| | | |
|---|---|---|
| 2011/0074246 A1 | 3/2011 | Nishie et al. |
| 2011/0115337 A1 | 5/2011 | Nakamua et al. |
| 2013/0223191 A1* | 8/2013 | Nakamura et al. ............ 367/135 |
| 2013/0258802 A1* | 10/2013 | Nakamura et al. ................ 367/7 |
| 2013/0258803 A1* | 10/2013 | Nakamura et al. ................ 367/7 |
| 2013/0261465 A1* | 10/2013 | Nakamura et al. ............ 600/459 |
| 2014/0103781 A1* | 4/2014 | Nakamura et al. ............ 310/334 |

FOREIGN PATENT DOCUMENTS

| | | |
|---|---|---|
| JP | 2010-210283 A | 9/2010 |
| JP | 4618165 B2 | 1/2011 |
| JP | 2011-077918 A | 4/2011 |
| JP | 2011-082624 A | 4/2011 |
| JP | 2011-124973 A | 6/2011 |
| WO | WO 2013145763 A1 * | 10/2013 |
| WO | WO 2013145764 A1 * | 10/2013 |

* cited by examiner

ULTRASONIC TRANSDUCER ELEMENT CHIP, PROBE, ELECTRONIC INSTRUMENT, AND ULTRASONIC DIAGNOSTIC DEVICE

CROSS-REFERENCE TO RELATED APPLICATIONS

This application claims priority to Japanese Patent Application No. 2012-078673 filed on Mar. 30, 2012. The entire disclosure of Japanese Patent Application No. 2012-078673 is hereby incorporated herein by reference.

BACKGROUND

1. Technical Field

The present invention relates to an ultrasonic transducer element chip, a probe that uses the ultrasonic transducer element chip, and an electronic instrument and an ultrasonic diagnostic device and the like that use the probe.

2. Related Art

As described in Japanese Laid-Open Patent Publication No. 2011-82624, for example, an ultrasonic transducer element chip is provided with a substrate. A plurality of openings are formed in the substrate. An ultrasonic transducer element is provided in each of the openings. The ultrasonic transducer element is provided with a vibrating film. The vibrating film covers the openings from a surface of the substrate.

SUMMARY

When the openings are formed in the substrate, the strength of the substrate is deteriorated. The strength is insufficient with respect to force in a thickness direction of the substrate. Therefore, when the ultrasonic transducer element chip is pressed against a target to be tested, the ultrasonic transducer element chip was sometimes damaged.

According to at least one embodiment of the present invention, an ultrasonic transducer element chip that is thin and has sufficient strength in resistance to pressing force in a thickness direction of a substrate can be provided.

According to one aspect of the present invention, an ultrasonic transducer element chip includes a substrate, a plurality of ultrasonic transducer elements and a reinforcing member. The substrate defines a plurality of openings arranged in an array pattern. The ultrasonic transducer elements are respectively disposed at the openings on a first surface of the substrate. The reinforcing member is fixed on a second surface of the substrate opposite to the first surface of the substrate to reinforce the substrate. The reinforcing member includes a plurality of linear groove parts formed on a surface of the reinforcing member fixed on the second surface of the substrate so that internal spaces of the openings and an external space of the substrate are in communication with each other via the linear groove parts. The linear groove parts extend along a plane of the surface of the reinforcing member. The linear groove parts are arranged at an interval in a first direction smaller than a width of each of the openings on the second surface of the substrate in the first direction.

In this kind of ultrasonic transducer element chip, the ultrasonic transducer elements can be formed to be thin. The ultrasonic transducer elements can be formed in a thin substrate. Even in a case where the reinforcing member is fixed to a substrate, the ultrasonic transducer element chip can be formed to be thin. In addition, since the reinforcing member is fixed on the second surface of the substrate, it is possible for the strength of the substrate to be reinforced in the substrate thickness direction. The internal spaces of the openings are enclosed by the substrate, the ultrasonic transducer element, and the reinforcing member. The linear groove parts connect the internal spaces of the openings and the external space of the substrate to each other. In this way, it is possible to ensure ventilation between the internal space of each opening and outside of the internal space. If the linear groove parts are arranged at intervals smaller than the width of the opening in the first direction, then even if relative positional displacement occurs between the substrate and the reinforcing member, it is possible to have at least one linear groove part connected to the opening. It is possible to absolutely ensure ventilation to the outside the opening for each opening. The internal spaces of the openings are not sealed tight. The internal spaces of the openings can easily follow ambient pressure fluctuations. In this way, it is possible to reliably avoid damage to the ultrasonic transducer element. If by chance the internal spaces of the openings are sealed airtight, there will be concern for damage to the ultrasonic transducer element due to pressure fluctuations.

The reinforcing member may be bonded to a partition wall section of the substrate between the openings in at least one bonding region. When the partition wall section is bonded to the reinforcing member, the movement of the partition wall section is restricted by the reinforcing member. Thus, vibration of the partition wall section can be prevented. As a result, crosstalk between the ultrasonic transducer elements can be prevented. Further, when the movement of the partition wall section is restricted, it is possible to avoid having the vibration of the partition wall section act on the ultrasonic vibration of the ultrasonic transducer elements. Then, ultrasonic vibration in a clear vibration mode can be obtained in the ultrasonic transducer elements. Consequently, when vibration of the partition wall section is avoided in this way, it is possible to inhibit a decrease in the amplitude of ultrasonic vibration.

With the ultrasonic transducer element chip, in a plan view seen along a substrate thickness direction, each of the linear groove parts may continuously extend across each of a plurality of the openings in a corresponding one of a plurality of columns of the array pattern so that the internal spaces of adjacent ones of the openings in the corresponding one of the columns of the array pattern are in communication with each other and the internal space of one of the openings disposed at an end of the corresponding one of the columns is in communication with the external space disposed outside of an outline of the substrate. In this way, it is possible to ensure ventilation for all the openings of one column.

With the ultrasonic transducer element chip, instead of the one linear groove part, in a plan view seen along a substrate thickness direction, a combination of a plurality of the linear groove parts may extend across each of a plurality of the openings in a corresponding one of a plurality of columns of the array pattern so that the internal spaces of adjacent ones of the openings in the corresponding one of the columns of the array pattern are in communication with each other and the internal space of one of the openings disposed at an end of the corresponding one of the columns is in communication with the external space disposed outside of an outline of the substrate. In this way, it is possible to ensure ventilation for all the openings of one column.

The interval in the first direction at which the linear groove parts may be arranged is $1/3$ or greater than and smaller than $1/2$ of the width of each the openings in the first direction. If the linear groove parts are aligned at this kind of interval, even if clogging occurs with one linear groove part, for example, it is possible to ensure ventilation between the outside of the openings with the other linear groove parts.

In a plan view seen along a substrate thickness direction, the openings may have rectangular outlines, and the linear groove parts extend across the openings along a short side direction of the rectangle outlines. When the intervals between the linear groove parts are set in the long side direction of the rectangle in this way, it is possible to ensure a larger interval between parallel lines compared to when the intervals between the linear groove parts are set in the short side direction of the rectangle. Therefore, it is possible to form a smaller number of linear groove parts. This makes it possible to achieve more efficient processing.

In a plan view seen along a substrate thickness direction, the openings may have rectangular outlines, and the linear groove parts extend across the openings along a long side direction of the rectangle outlines. The wall of the outline of the opening does not deform easily due to the aspect ratio with the short side of the rectangle. Even if the superimposition scope becomes narrow based on the shape of the linear groove parts, it is possible maintain a relatively high rigidity for the wall. Therefore, it is possible to inhibit vibration of the wall.

In a plan view seen along a substrate thickness direction, the openings may be arranged at a constant pitch in the first direction, and the linear groove parts are arranged at a regular pitch in the first direction. When forming the linear groove parts, as long as a regular pitch between the linear groove parts is ensured, it is possible to freely set the relative position of the linear groove parts and the reinforcing member. For processing of the reinforcing member, it is possible to ease the alignment precision of the reinforcing member. This makes it possible to make the reinforcing member processing easier.

The ultrasonic transducer element chip may be incorporated in a probe. The probe may be provided with the ultrasonic transducer element chip, and a case member supporting the ultrasonic transducer element chip.

The probe may be incorporated in an electronic instrument. The electronic instrument may be provided with a probe, and a processing circuit connected to the probe and configured to process output signals of the ultrasonic transducer elements.

Similarly, the probe may be incorporated in an ultrasonic diagnostic device. The ultrasonic diagnostic device may be provided with a probe, a processing circuit connected to the probe, and configured to process output signals of the ultrasonic transducer elements to generate an image, and a display device configured to display the image.

The ultrasonic transducer element chip may be incorporated in a probe head. The probe head may be provided with an ultrasonic transducer element chip, and a case member supporting the ultrasonic transducer element chip, and configured to be coupled to a probe main body of a probe.

According to another aspect of the present invention, a method for manufacturing an ultrasonic transducer element chip includes: holding a reinforcing member including a plurality of linear groove parts formed on a surface of the reinforcing member and arranged at an interval in a first direction smaller than a width of each of a plurality of openings in the first direction, the openings being arranged in an array pattern on a substrate; and superimposing the surface of the reinforcing member and a second surface of the substrate opposite to a first surface of the substrate on which a plurality of ultrasonic transducer elements are respectively disposed at the openings.

When the interval of the linear groove parts are set in this way, even when relative positional displacement occurs between the substrate and the reinforcing member, it is possible for at least one linear groove part to be in communication with the openings. In addition, even in a case when the substrate and the reinforcing member are superimposed with each other in air or in another gas atmosphere, it is possible to achieve superimposing relatively easily. On the other hand, when the second surface of the substrate is superimposed on an even plane, gas is pressed into each opening interior by the plane of the reinforcing member. At atmospheric pressure, gas of greater volume than the volume of the space within the opening tries to remain inside the openings. If extra gas does not escape from the gap between the substrate and the reinforcing member at the same time as sealing off of the openings, it is not possible to achieve binding together of the substrate and the reinforcing member.

BRIEF DESCRIPTION OF THE DRAWINGS

Referring now to the attached drawings which form a part of this original disclosure.

DETAILED DESCRIPTION OF EXEMPLARY EMBODIMENTS

Next, embodiments of the present invention will be explained with reference to the attached drawings. The embodiments explained below shall not be construed as unreasonably limiting the subject matter of the present invention described in the claims, and all the elements explained in the embodiments are not necessarily essential to the solving means of the present invention.

(1) Overall Configuration of Ultrasonic Diagnostic Device

Figure 1:
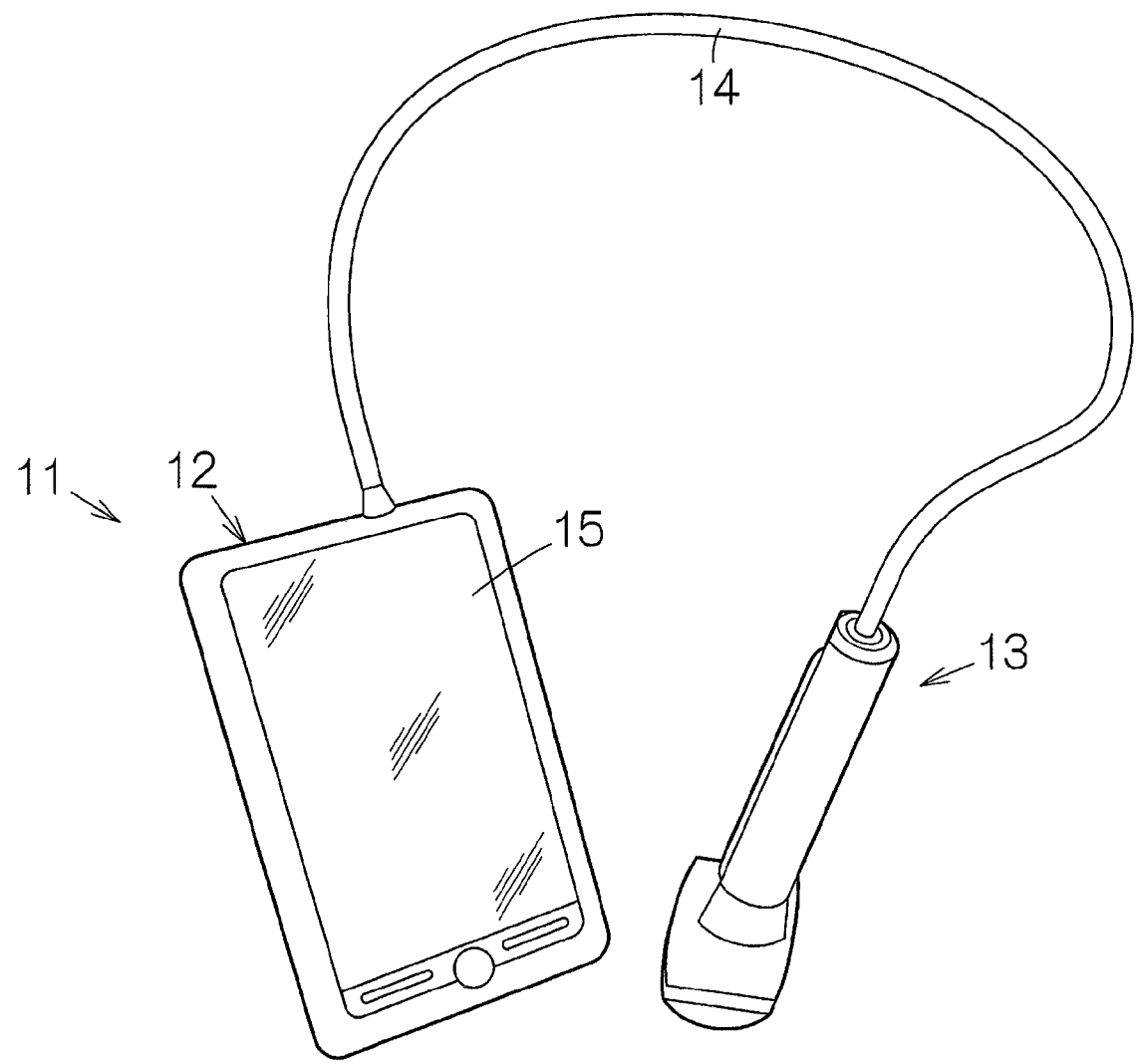
FIG. 1 is a perspective view schematically showing an example of an electronic instrument, that is, an ultrasonic diagnostic device according to one embodiment of the present invention.

FIG. 1 schematically shows a configuration of an ultrasonic diagnostic device 11 as an example of an electronic instrument according to an embodiment of the present invention. The ultrasonic diagnostic device 11 is provided with a device terminal 12 and an ultrasonic probe (probe) 13. The device terminal 12 and the ultrasonic probe 13 are connected to each other through a cable 14. The device terminal 12 and the ultrasonic probe 13 communicate an electric signal through the cable 14. A display panel (display device) 15 is incorporated in the device terminal 12. A screen of the display panel 15 is exposed on a surface of the device terminal 12. As described later, in the device terminal 12, an image is generated based on ultrasonic waves detected with the ultrasonic probe 13. Imaged detection results are displayed on the screen of the display panel 15.

Figure 2:
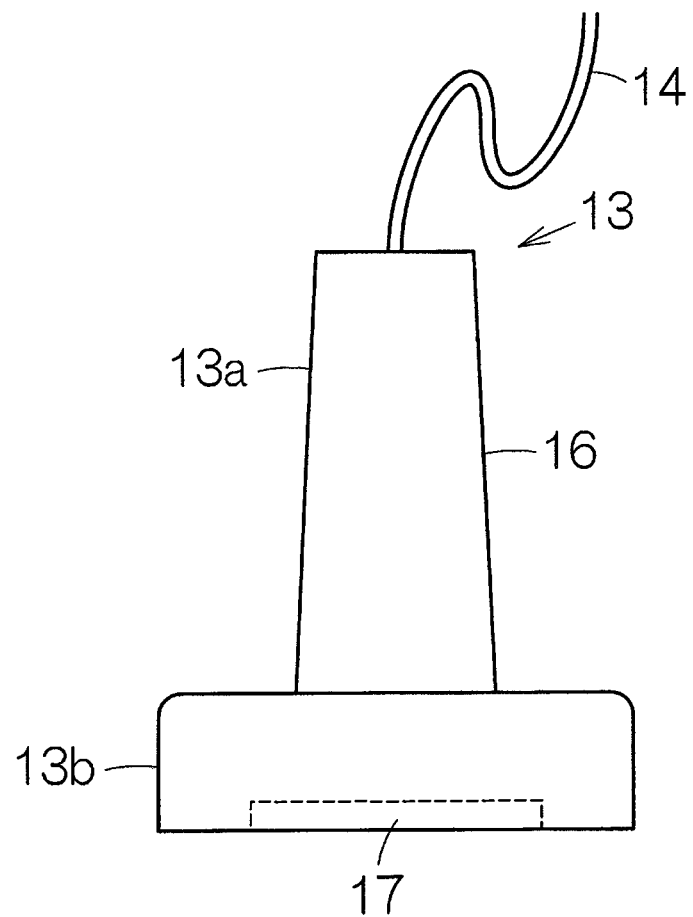
FIG. 2 is an enlarged front view of an ultrasonic probe.

As shown in FIG. 2, the ultrasonic probe 13 has a case 16 (one example of a case member). An ultrasonic transducer element chip (hereinafter referred to as "element chip") 17 is accommodated in the case 16. A surface of the element chip 17 may be exposed on a surface of the case 16. The element chip 17 outputs ultrasonic waves from the surface thereof, and receives reflected waves of ultrasonic waves. Also, the ultrasonic probe 13 may be provided with a probe head 13b removably coupled with a probe main body 13a. In such an instance, the element chip 17 may be incorporated in the case member of the probe head 13b, which is configured to be coupled to the probe main body 13a.

Figure 3:
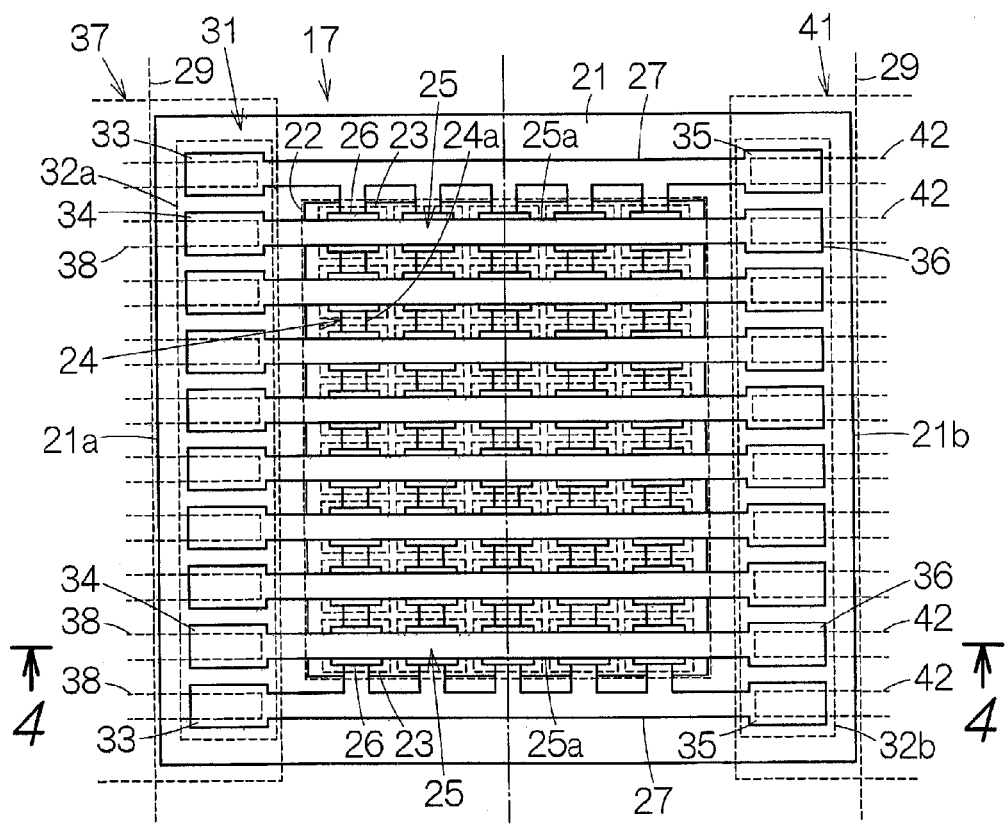
FIG. 3 is an enlarged plan view of an ultrasonic transducer element chip.

FIG. 3 schematically shows a plan view of the element chip 17. The element chip 17 is provided with a substrate 21. An element array 22 is formed on the substrate 21. The element array 22 is constructed with an arrangement of ultrasonic transducer elements (hereinafter referred to as "elements") 23. The arrangement is formed in a matrix having a plurality of rows and a plurality of columns. Each element 23 has a piezoelectric element section. The piezoelectric element section is constructed of a lower electrode 24, an upper electrode 25, and a piezoelectric film 26. The piezoelectric film 26 is sandwiched between the lower electrode 24 and the upper electrode 25 in each element 23.

The lower electrode 24 has a plurality of first conductive bodies 24a. The first conductive bodies 24a extend in a column direction of the arrangement in parallel to each other. One first conductive body 24a is assigned to each column of the elements 23. One first conductive body 24a is provided in common with respect to the piezoelectric films 26 of the elements 23 aligned in the column direction of the arrangement. Both ends of the first conductive body 24a are connected to a pair of extraction wirings 27, respectively. The extraction wirings 27 extend in a row direction of the arrangement in parallel to each other. Therefore, all the first conductive bodies 24a have the same length. In this manner, the lower electrode 24 is provided in common with respect to the elements 23 of the entire matrix.

The upper electrode 25 has a plurality of second conductive bodies 25a. The second conductive bodies 25a extend in a row direction of the arrangement in parallel to each other. One second conductive body 25a is assigned to each row of the elements 23. One second conductive body 25a is provided in common with respect to the piezoelectric films 26 of the elements 23 aligned in the row direction of the arrangement. Power distribution to the elements 23 is switched for each row. Line scanning or sector scanning is achieved corresponding to such switching of power distribution. Since the elements 23 in one row output ultrasonic waves at the same time, the number of the elements 23 in one row, that is, the number of columns of the arrangement can be determined based on the output level of ultrasonic waves. For example, the number of columns may be set to be around 10-15. In the drawing, five columns are illustrated for simplicity. The number of rows of the arrangement can be determined based on the extent of an area to be scanned. For example, the number of rows may be set to be 128 or 256. In the drawing, eight rows are illustrated for simplicity. Regarding the arrangement, a zigzag pattern may be used. In the zigzag pattern, a group of the elements 23 in an even row may be displaced with respect to a group of the elements 23 in an odd row by one-half of the column pitch. The number of the elements in one of an odd row and an even row may be smaller than the number of the elements in the other of an odd row and an even row by one. Furthermore, the role of the lower electrode 24 and the role of the upper electrode 25 may be switched. Specifically, the upper electrode may be connected in common to the elements 23 of the entire matrix, and the lower electrode may be connected in common to the elements 23 in each row of the arrangement.

The outline of the substrate 21 has a first side 21a and a second side 21b that are opposed and partitioned by a pair of straight lines 29 parallel to each other. In the peripheral region 31 that extends between the outline of the element array 22 and the outer edge of the substrate 21, a first terminal array 32a of one line is arranged between the first side 21a and the outline of the element array 22, and a second terminal array 32b of one line is arranged between the second side 21b and the outline of the element array 22. One line of the first terminal array 32a can be formed parallel to the first side 21a. One line of the second terminal array 32b can be formed parallel to the second side 21b. The first terminal array 32a is constructed of a pair of lower electrode terminals 33 and a plurality of upper electrode terminals 34. Similarly, the second terminal array 32b is constructed of a pair of lower electrode terminals 35 and a plurality of upper electrode terminals 36. The lower electrode terminals 33 and 35 are connected to both ends of each of the extraction wiring 27, respectively. It is sufficient for the extraction wirings 27 and the lower electrode terminals 33 and 35 to be formed plane-symmetrically with respect to a vertical plane that bisects the element array 22. The upper electrode terminals 34 and 36 are connected to both ends of each of the second conductive bodies 25a, respectively. It is sufficient for the second conductive bodies 25a, the upper electrode terminals 34 and 36 to be formed plane-symmetrically with respect to the vertical plane that bisects the element array 22. Here, the outline of the substrate 21 is formed in a rectangle. The outline of the substrate 21 may also be square or trapezoidal.

A first flexible printed substrate 37 is coupled with the substrate 21. The first flexible printed circuit 37 covers the first terminal array 32a. Conductive lines, that is, first signal lines 38 are formed at one end of the first flexible printed circuit 37 corresponding to the lower electrode terminals 33 and the upper electrode terminals 34, respectively. The first signal lines 38 are respectively opposed to the lower electrode terminals 33 and the upper electrode terminals 34, and respectively bonded thereto. Similarly, a second flexible printed substrate 41 covers the substrate 21. The second flexible printed circuit 41 covers the second terminal array 32b. Conductive lines, that is, second signal lines 42 are formed at a first end 41a of the second flexible printed circuit 41 corresponding to the lower electrode terminals 35 and the upper electrode terminals 36, respectively. The second signal lines 42 are respectively opposed to the lower electrode terminals 35 and the upper electrode terminals 36, and respectively bonded thereto.

Figure 4:
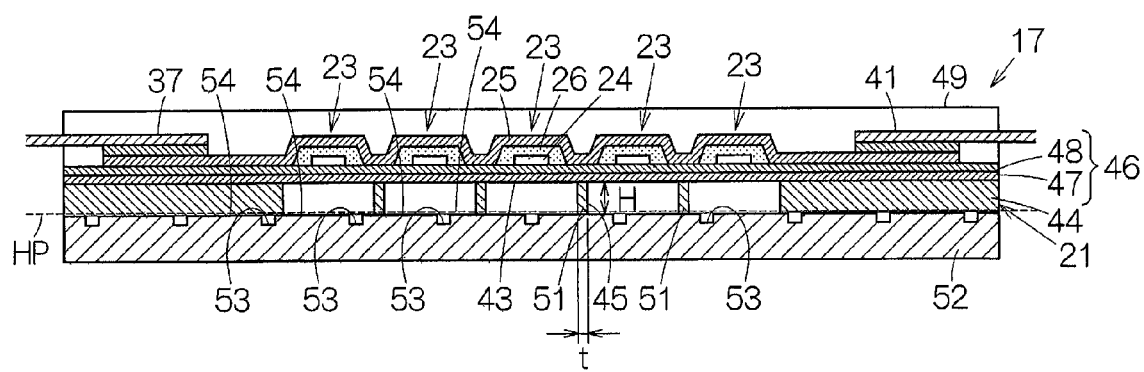
FIG. 4 is a sectional view along line 4-4 of FIG. 3.

As shown in FIG. 4, each of the elements 23 has a vibrating film 43. When constructing the vibrating film 43, an opening 45 is formed in each of the elements 23 on a substrate base 44 of the substrate 21. The openings 45 are arranged in an array pattern with respect to the substrate base 44. A flexible film 46 is formed on the entire surface of the substrate base 44. The flexible film 46 is constructed of a silicon oxide (SiO$_2$) layer 47 layered on the surface of the substrate base 44, and a zirconium oxide (ZrO$_2$) layer 48 layered on a surface of the silicon oxide layer 47. The flexible film 46 contacts the openings 45. In this manner, a part of the flexible film 46 serves as the vibrating film 43 corresponding to the outline of the opening 45. The film thickness of the silicon oxide layer 47 can be determined based on the resonance frequency.

The lower electrode 24, the piezoelectric film 26, and the upper electrode 25 are layered on a surface of the vibrating film 43 in this order. For the lower electrode 24, a layered film of titanium (Ti), iridium (Ir), platinum (Pt), and titanium (Ti) can be used, for example. The piezoelectric film 26 may be formed of piezoelectric zirconate titanate (PZT), for example. The upper electrode 25 may be formed of iridium (Ir), for example. Another conductive material may be used for the lower electrode 24 and the upper electrode 25, and another piezoelectric material may be used for the piezoelectric film 26. Here, the piezoelectric film 26 completely covers the lower electrode 24 under the upper electrode 25. The function of the piezoelectric film 26 prevents short circuits between the upper electrode 25 and the lower electrode 24.

A protective film 49 is layered on the surface of the substrate 21. The protective film 49 covers, for example, the entire surface of the substrate 21. As a result, the protective film 49 covers the element array 22, the first terminal array 32a, the second terminal array 32b, and the first flexible printed circuit 37 and the second flexible printed circuit 41. For example, a silicone resin film may be used for the protective film 49. The protective film 49 protects the configuration of the element array 22, the bonding of the first terminal array 32a and the first flexible printed circuit 37, and the bonding of the second terminal array 32b and the second flexible printed circuit 41.

Partition walls 51 are laid out between the adjacent openings 45. The openings 45 are partitioned by the partition walls 51. The wall thickness "t" of the partition wall 51 corresponds to the interval between the hollow spaces of the openings 45. The partition wall 51 defines two wall surfaces in planes extending in parallel to each other. The wall thickness "t" of the partition wall 51 corresponds to the interval between the wall surfaces. Specifically, the wall thickness "t" can be defined by the length of a vertical line that is orthogonal to the wall surfaces and sandwiched between the wall surfaces. The wall height "H" of the partition wall 51 corresponds to the depth of the opening 45. The depth of the opening 45 corresponds to the thickness of the substrate base 44. Therefore, the wall height "H" of the partition wall 51 can be defined as the length of the wall surface defined in the thickness direction of the substrate base 44. Since the substrate base 44 has a uniform thickness, the partition wall 51 can have a uniform wall height "H" over the entire length. When the wall thickness "t" of the partition wall 51 is decreased, the arrangement density of the vibrating film 43 can be increased. This can contribute to downsizing of the element chip 17. When the wall height "H" of the partition wall 51 is larger than the wall thickness "t", the bending rigidity of the element chip 17 can be increased. Consequently, the interval between the openings 45 is set to be smaller than the depth of the opening 45.

A reinforcing plate (reinforcing member) 52 is fixed to a reverse surface of the substrate base 44. The reverse surface of the substrate base 44 is overlaid on a surface of the reinforcing plate 52. The reinforcing plate 52 closes the openings 45 in a reverse surface of the element chip 17. The reinforcing plate 52 may have a rigid base material. For example, the reinforcing plate 52 may be formed of a silicon substrate. The plate thickness of the substrate base 44 is set to be around 100 μm, and the plate thickness of the reinforcing plate 52 is set to be around 100-150 μm. Here, the partition walls 51 are bonded to the reinforcing plate 52. The reinforcing plate 52 is bonded to each of the partition walls 51 in at least one bonding region. An adhesive can be used for bonding.

Linear grooves (linear groove parts) 53 are formed on the surface of the reinforcing plate 52. The grooves 53 divide the surface of the reinforcing plate 52 into a plurality of planes 54. The plurality of planes 54 expand within one hypothetical plane HP. The reverse surface of the substrate base 44 expands within that hypothetical plane HP. The partition wall 51 is bonded to the plane 54. The grooves 53 sink from the hypothetical plane HP. The cross section shape of the groove 53 can be a quadrangle, a triangle, a semi-circle or another shape.

Figure 5:
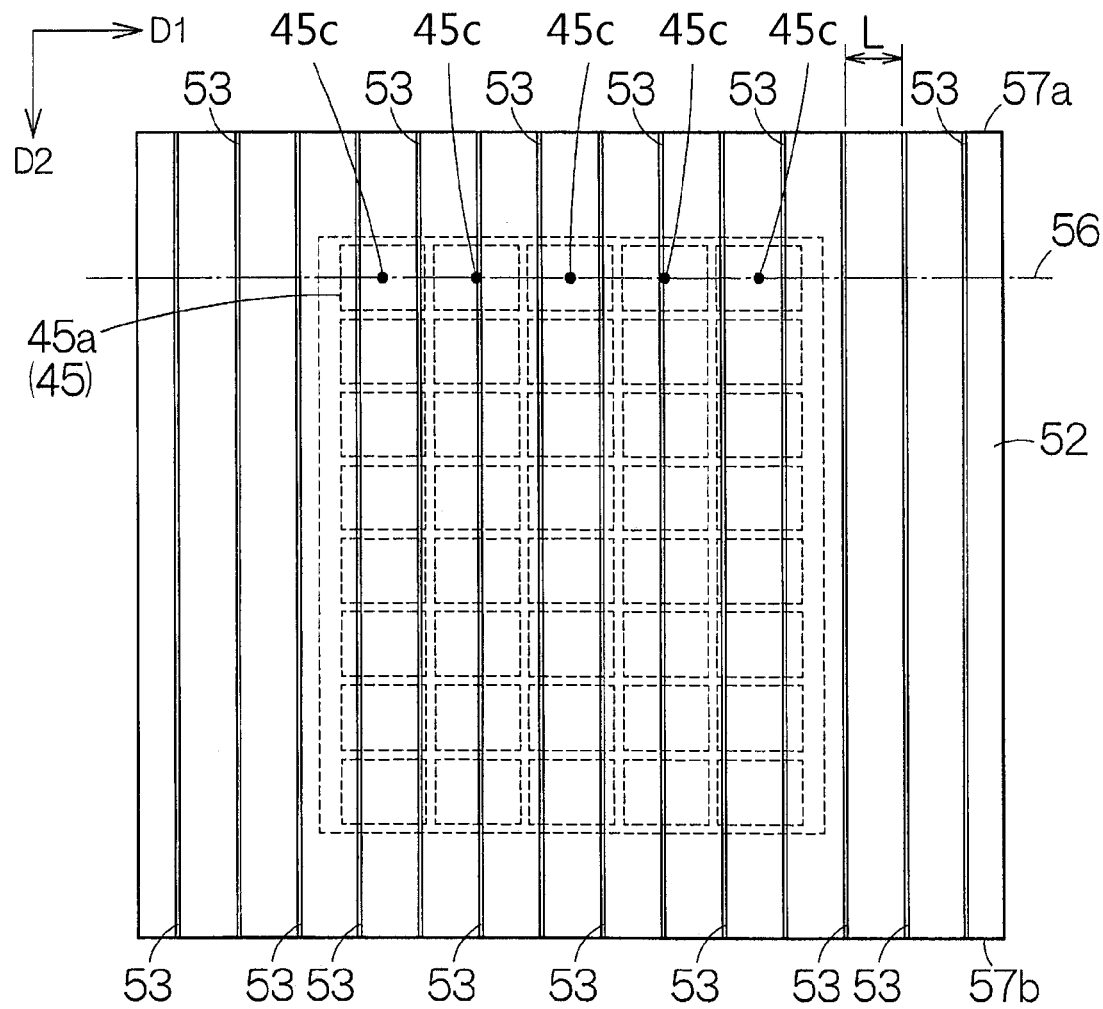
FIG. 5 is a plan view of a reinforcing plate showing grooves.

As shown in FIG. 5, the openings 45 form a line in a first direction D1. The centroids 45c of the outline shapes of the openings 45 are arranged at an equal pitch on a straight line 56 in the first direction D1. Since the outlines 45a of the openings 45 are formed by copying a single shape, the openings 45 of the same shape are arranged repeatedly at a uniform pitch. For example, an outline 45a of the opening 45 is defined as a quadrangle. Specifically, it is formed in a rectangle. The long side of the rectangle is made to coincide with the first direction D1. Since the opening 45 has a rectangular outline 45a in this way, the partition wall 51 can have a uniform wall thickness "t" over the entire length. In such an instance, the bonding region of the partition walls 51 may be a region that includes a center position of the long side. In particular, the bonding region of the partition walls 51 may be a region that includes the entire length of the long side. The partition walls 51 may be surface-bonded to the reinforcing plate 52 with respect to the entire surface between the openings 45 over the entire length of the long side. Also, the bonding region of the partition walls 51 may be located in at least one position of each side of the quadrangle. The bonding region of the partition walls 51 may continuously surround the quadrangle. The partition walls 51 may be surface-bonded to the reinforcing plate 52 with respect to the entire surface between the openings 45 over the entire periphery of the quadrangle.

The grooves 53 are aligned in the first direction D1 mutually parallel at a fixed interval L. The grooves 53 extend in a second direction D2 that intersects with the first direction D1. Both ends of the grooves 53 open at the end surfaces 57a and 57b of the reinforcing plate 52. One groove 53 cuts across one line (here it is one column) of outlines 45a of the openings 45 in sequence. Each of the openings 45 has at least one groove 53 connected. Here, the second direction D2 is orthogonal to the first direction D1. Therefore, the grooves 53 cut across the outlines 45a of the openings 45 in the short side direction of the rectangle.

Figure 6:
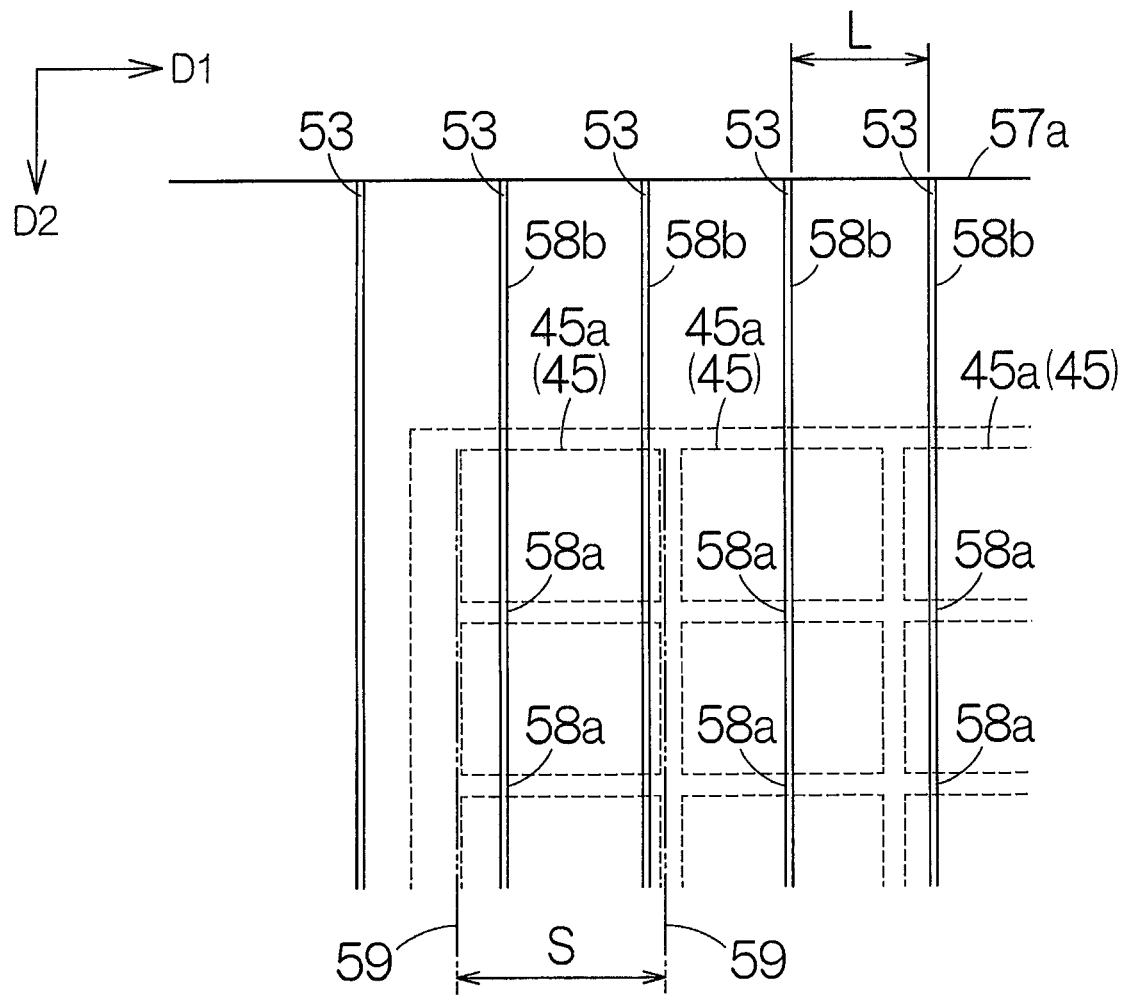
FIG. 6 is an enlarged partial plan view of FIG. 5.

As shown in FIG. 6, between the planes 54, the grooves 53 form passages 58a and 58b between the substrate base 44 and the reinforcing plate 52. In this way, the space within the groove 53 is made to communicate with the internal space of the opening 45. The passages 58a and 58b ensure ventilation between the internal spaces of the openings 45 and the external space of the substrate 21. In a plan view seen from the direction orthogonal to the surface of the substrate 21, specifically, the thickness direction of the substrate 21, one groove 53 cuts across one line (here it is one column) of the outlines 45a of the openings 45 in sequence, so the openings 45 are connected successively by the passage 58a. Both ends of the groove 53 are open at the end surfaces 57a and 57b of the reinforcing plate 52. In this way, the passage 58b opens from the opening 45 of the line end to outside the outline of the substrate 21.

The interval L of the grooves 53 is set to be smaller than the opening width S of the opening 45. The opening width S is defined by the maximum length among the cross cutting lines of the openings 45 in the direction in which the grooves 53 are aligned, specifically, the first direction D1. In other words, the opening width S correlates to the interval between the parallel lines 59 circumscribing the outlines 45a of the openings 45. The parallel lines 59 circumscribing the outlines 45a of the openings 45 are specified for each opening 45. The parallel lines 59 extend in the second direction D2. In cases when the opening widths S are mutually different for each opening 45, the grooves 53 can be aligned at intervals L that are smaller than the minimum value of the opening widths S. Here, the interval L of the grooves 53 is set to be ⅓ or greater and less than ½ the opening width S of the opening 45.

(2) Circuit Configuration of Ultrasonic Diagnostic Device

Figure 7:
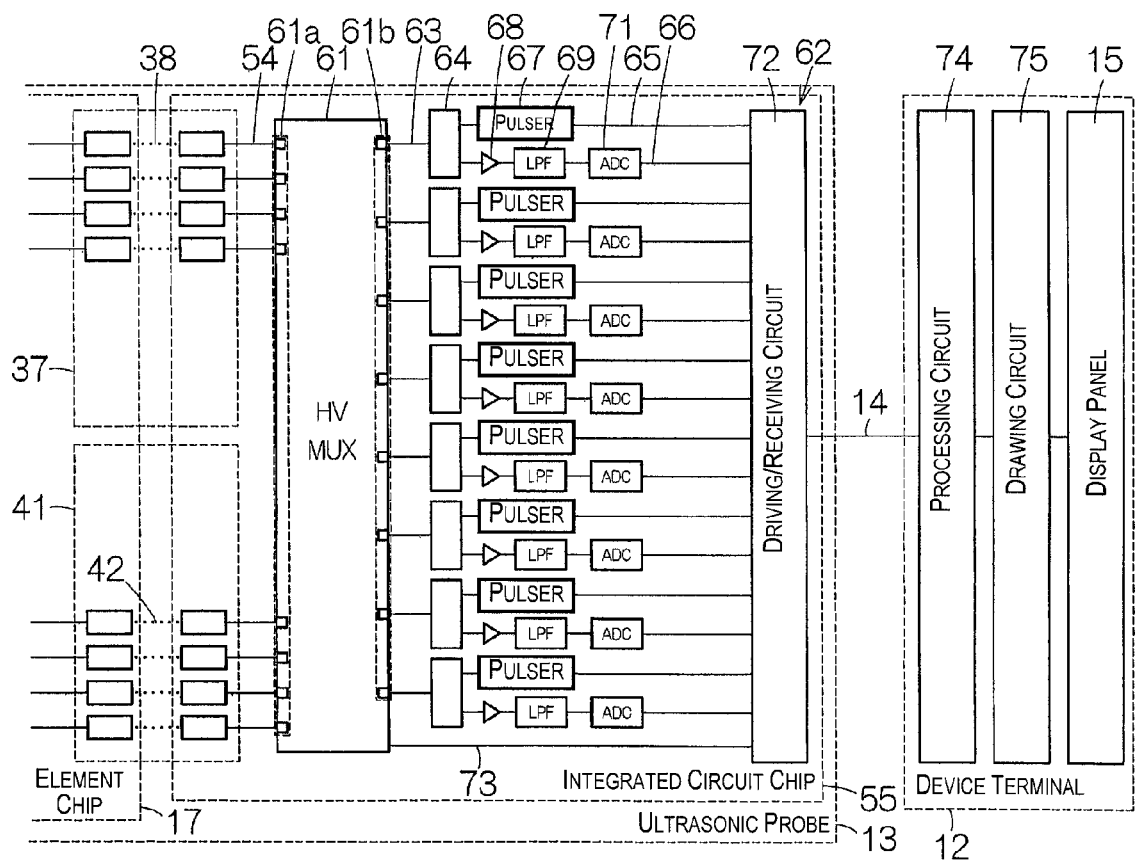
FIG. 7 is a block diagram schematically showing a circuit configuration of the ultrasonic diagnostic device.

As shown in FIG. 7, an integrated circuit has a multiplexer 61, and a transmitting and receiving circuit 62. The multiplexer 61 has a group of ports 61a on the element chip 17 side, and a group of ports 61b on the transmitting and receiving circuit 62 side. The first signal lines 38 and the second signal lines 42 are connected to the group of ports 61a via first wirings 54. In this manner, the group of ports 61a are connected to the element array 22. A prescribed number of signal lines 63 within the integrated circuit chip 55 are connected to the group of ports 61b on the transmitting and receiving circuit 62 side. The prescribed number corresponds to the number of rows of the elements 23 output simultaneously when scanning. The multiplexer 61 controls interconnection between the ports on the cable 14 side and the ports on the element chip 17 side.

The transmitting and receiving circuit 62 has a prescribed number of changing switches 64. The changing switches 64 are connected to the corresponding signal lines 63, respectively. The transmitting and receiving circuit 62 has a transmission channel 65 and a reception channel 66 for each of the changing switches 64. The transmission channel 65 and the reception channel 66 are connected to the changing switch 64 in parallel. The changing switch 64 selectively connects the transmission channel 65 and the reception channel 66 to the multiplexer 61. A pulser 67 is incorporated in the transmission channel 65. The pulser 67 outputs a pulse signal at a frequency corresponding to the resonance frequency of the vibrating film 43. An amplifier 68, a low-pass filter (LPF) 69, and an analog-digital converter (ADC) 71 are incorporated in the reception channel 66. A detection signal of each of the elements 23 is amplified, and converted into a digital signal.

The transmitting and receiving circuit 62 has a driving/receiving circuit 72. The transmission channel 65 and the reception channel 66 are connected to the driving/receiving circuit 72. The driving/receiving circuit 72 controls the pulser 67 simultaneously depending on the state of scanning. The driving/receiving circuit 72 receives a digital signal of a detection signal depending on the state of scanning. The driving/receiving circuit 72 is connected to the multiplexer 61 through a control line 73. The multiplexer 61 conducts control of interconnection based on a control signal supplied from the driving/receiving circuit 72.

A processing circuit 74 is incorporated in the device terminal 12. The processing circuit 74 can be provided with a central processing unit (CPU) 74 and a memory, for example. The entire operation of the ultrasonic diagnostic device 11 is controlled in accordance with processing of the processing circuit 74. The processing circuit 74 controls the driving/receiving circuit 72 in accordance with instructions input by a user. The processing circuit 74 generates an image in accordance with a detection signal of the element 23. The image is specified by drawing data.

A drawing circuit 75 is incorporated in the device terminal 12. The drawing circuit 75 is connected to the processing circuit 74. The display panel 15 is connected to the drawing circuit 75. The drawing circuit 75 generates a driving signal in accordance with drawing data generated in the processing circuit 74. The driving signal is sent to the display panel 15. As a result, an image is displayed on the display panel 15.

(3) Operation of Ultrasonic Diagnostic Device

Next, the operation of the ultrasonic diagnostic device 11 will be explained briefly. The processing circuit 74 gives the driving/receiving circuit 72 instructions to transmit and receive ultrasonic waves. The driving/receiving circuit 72 supplies a control signal to the multiplexer 61, and supplies a driving signal to each of the pulsers 67. The pulser 67 outputs a pulse signal in response to the supply of the driving signal. The multiplexer 61 connects the port of the group of ports 61a to the port of the group of ports 61b in response to the instructions of the control signal. The pulse signal is supplied to the elements 23 for each row through the lower electrode terminals 33, 35 and the upper electrode terminals 34, 36 in response to the selection of the port. The vibrating film 43 vibrates in response to the supply of the pulse signal. As a result, desired ultrasonic waves are emitted toward a target (for example, the inside of a human body).

After ultrasonic waves are transmitted, the changing switch 64 is switched. The multiplexer 61 maintains the connection relation of the ports. The changing switch 64 establishes a connection between the reception channel 66 and the signal line 63 instead of a connection between the transmission channel 65 and the signal line 63. Reflected waves of ultrasonic waves vibrate the vibrating film 43. As a result, a detection signal is output from the element 23. The detection signal is converted into a digital signal, and sent into the driving/receiving circuit 72.

Transmission and reception of ultrasonic waves are repeated. For repeating transmission and reception of ultrasonic waves, the multiplexer 61 changes the connection relation of the ports. As a result, line scanning or sector scanning is achieved. When scanning is finished, the processing circuit 74 generates an image based on the digital signal of the detection signal. The generated image is displayed on the screen of the display panel 15.

In the element chip 17, the element 23 can be formed to be thin. The element 23 can be formed on the thin substrate 21. Even in a case where the reinforcing plate 52 is fixed to the substrate 21, the element chip 17 can be formed to be thin. At the same time, the reinforcing plate 52 reinforces the strength of the substrate 21. In particular, since the wall thickness "t" is smaller than the wall height "H" in the partition wall 51, sufficient rigidity of the partition wall 51 can be obtained in the thickness direction of the substrate 21 due to the section modulus. Force in the thickness direction of the substrate 21 is transmitted through the partition wall 51 and supported by the reinforcing plate 52. In this manner, the element chip 17 has sufficient strength in the thickness direction of the substrate 21. Even when the plate thickness of the substrate 21 is set to be around 100 μm, for example, the reinforcing plate 52 can prevent the substrate 21 from being damaged. On the other hand, in a case where the element array is constructed of a bulk-type ultrasonic transducer element, the plate thickness of the substrate is set to be around several millimeters. Even when the reinforcing plate 52 is bonded, for example, the thickness of the element chip 17 can be reduced securely compared to the case where the element array is constructed of a bulk-type ultrasonic transducer element. In addition, since the acoustic impedance of the vibrating film 43 is close to that of a human body compared to a bulk-type ultrasonic transducer element, an acoustic impedance matching layer can be omitted in the element chip 17 unlike in the case of a bulk-type ultrasonic transducer element. Omission of the matching layer can further contribute to making the element chip 17 thinner.

The reinforcing plate 52 is bonded to each of the partition walls 51 in at least one bonding region. When the partition walls 51 are bonded to the reinforcing plate 52, the movement of the partition walls 51 is restricted by the reinforcing plate 52. Thus, vibration of the partition walls 51 can be prevented. As a result, crosstalk between the elements 23 can be prevented. Further, when the movement of the partition walls 51 is restricted, vibration of the partition walls 51 can be prevented from acting on ultrasonic vibration of the elements 23. Then, ultrasonic vibration in a clear vibration mode can be obtained in the elements 23. When vibration of the partition walls 51 is avoided, the amplitude of ultrasonic vibration can be prevented from being decreased. On the other hand, when the partition wall 51 moves, a distorted vibration mode having a lower frequency than the vertical vibration mode of the vibrating film 43 occurs. Furthermore, the kinetic energy of the vibrating film 43 decreases by the movement amount of the partition wall 51, and the amplitude of the vibration decreases.

The spaces within the openings 45 are enclosed by the flexible film 46 (vibrating film 43) and the reinforcing plate 52. In a plan view seen from the substrate 21 thickness direction, the grooves 53 cut across the outlines 45a of the openings 45. In this way, it is possible to ensure ventilation between the internal space of each opening 45 and the external space of the substrate 21. As a result, the internal spaces of the openings 45 are connected to the atmospheric space. This makes it possible to avoid a rise in pressure in the internal spaces of the openings 45. That makes it possible to prevent damage to the vibrating film 43. Here, the external space is the space separated from the internal space by the substrate 21, the flexible film 46, and the reinforcing plate 52, meaning that this is a significantly larger space than the internal space.

The interval L of the grooves 53 are set to be smaller than the opening width S of the openings 45 with the element chip 17. Therefore, even when a relative position displacement occurs between the substrate 21 and the reinforcing plate 52, at least one groove 53 can be connected to the outlines 45a of the openings 45. It is possible to absolutely ensure ventilation to outside of the opening 45 for each of the openings 45. In addition, the interval L of the grooves 53 are set to be ⅓ or greater and less than ½ of the opening width S, so it is possible for at least two grooves 53 to be connected to the outlines 45a of the openings 45 for each opening 45. Therefore, with each opening 45, even if clogging occurs with one of the grooves 53, for example, it is possible to ensure ventilation between the other grooves 53 and outside of the openings 45. In fact, since cutting across more than four outlines 45a by the grooves 53 is avoided, it is possible to inhibit a decrease in bonding strength of the partition walls 51. Here, it is desirable for the width of the grooves 53 to be set smaller than the wall thickness "t" of the partition wall 51. By working in this way, even if the groove 53 is arranged between adjacent openings 45 in the first direction D1, it is possible to ensure a bonded surface of a sufficient size between the partition wall 51 and the reinforcing plate 52. This makes it possible to inhibit a decrease in the bonding strength of the partition walls 51.

The bonding region of the partition walls 51 can be a region that includes a center position of the long side. Therefore, a part of the partition walls 51 in which the amplitude of vibration is large is bonded to the reinforcing plate 52. As a result, vibration of the partition walls 51 can be effectively prevented. Also, the bonding region of the partition walls 51 can be a region that includes the entire length of the long side. When the partition walls 51 are bonded to the reinforcing plate 52 over the entire length of the long side, vibration of the partition walls 51 can be securely prevented. Further, the partition walls 51 can be surface-bonded with respect to the entire surface between the openings 45 over the entire length of the long side. When the partition walls 51 are surface-bonded to the reinforcing plate 52 with respect to the entire surface between the openings 45 over the entire length of the long side, vibration of the partition walls 51 can be securely prevented.

It is sufficient that the bonding region of the partition walls 51 be located in at least one position of each side of the quadrangle. When the partition walls 51 are bonded to the reinforcing plate 52 in each side of the quadrangle, vibration of the partition walls 51 can be securely prevented. Also, the bonding region of the partition walls 51 can continuously surround the quadrangle. When the partition walls 51 are bonded to the reinforcing plate 52 with respect to the entire region of the quadrangle, vibration of the partition walls 51 can be securely prevented. Further, the partition walls 51 can be surface-bonded with respect to the entire surface between the openings 45 over the entire periphery of the quadrangle. When the partition walls 51 are surface-bonded to the reinforcing plate 52 with respect to the entire surface between the openings 45 over the entire periphery of the quadrangle, vibration of the partition walls 51 can be securely prevented.

With the element chip 17, between adjacent openings 45 in the column direction, the spaces inside the openings 45 are in mutual communication by the passage 55a. Also, the passage 55b is open from the opening 45 of the column end to outside the outline of the substrate 21. The passages 55a and 55b are formed with one groove 53. In this way, it is possible to ensure ventilation for all of one column of openings 45 with one groove 53.

Further, the grooves 53 cut across the openings 45 in the short side direction of the rectangle in a plan view from the substrate 21 thickness direction. When the interval L between grooves 53 is set in this way in the long side direction of the rectangle, it is possible to ensure a larger interval between the parallel lines 56 compared to when the interval between the grooves 53 is set in the short side direction of the rectangle. Therefore, it is sufficient to form a smaller number of the grooves 53. This makes it possible to achieve more efficient processing.

In addition, the grooves 53 are aligned at an equal pitch in the first direction D1. When forming the grooves 53, as long as an equal pitch is ensured, it is possible to freely set the relative position of the groove 53 and the reinforcing plate 52. When processing the reinforcing plate 52, it is possible to ease the alignment precision of the reinforcing plate 52. This allows the processing of the reinforcing plate 52 to be made easier.

(4) Method for Manufacturing Ultrasonic Transducer Element Chip

Figure 8:
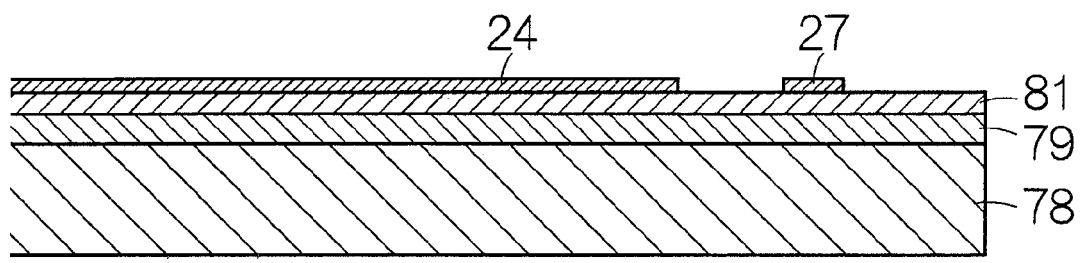
FIG. 8 is a partial enlarged vertical sectional view schematically showing a flexible film and a lower electrode formed on a silicon wafer.

As shown in FIG. 8, the lower electrode 24, the extraction wiring 27, and the lower electrode terminals 33, 35 (not shown in the drawings subsequent to FIG. 7) are formed on a surface of a silicon wafer (substrate) 78 for each element chip 17. Prior to forming the lower electrode 24, the extraction wiring 27, and the lower electrode terminals 33, 35, a silicon oxide film 79 and a zirconium oxide film 81 are formed on the surface of the silicon wafer 78 successively. A conductive film is formed on a surface of the zirconium oxide film 81. The conductive film is constructed as a layered film of titanium, iridium, platinum, and titanium. The lower electrode 24, the extraction wiring 27, and the lower electrode terminals 33, 35 are formed from the conductive film by a photolithographic technique.

Figure 9:
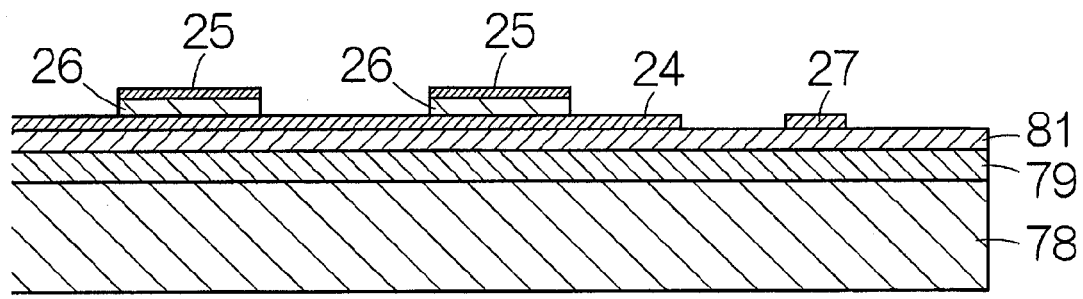
FIG. 9 is a partial enlarged vertical sectional view schematically showing a piezoelectric film and an upper electrode formed on the lower electrode.

As shown in FIG. 9, the piezoelectric film 26 and the upper electrode 25 are formed on a surface of the lower electrode 24 for each element 23. Prior to forming the piezoelectric film 26 and the upper electrode 25, a piezoelectric material film and a conductive film are formed on the surface of the silicon wafer 78. The piezoelectric material film is constructed of a PZT film. The conductive film is constructed of an iridium film. The piezoelectric film 26 and the upper electrode 25 are formed from the piezoelectric material film and the conductive film for each element 23 by a photolithographic technique.

Figure 10:
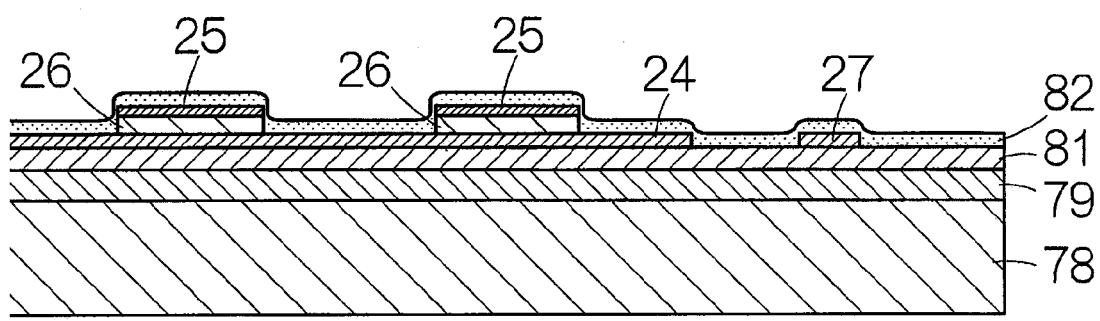
FIG. 10 is a partial enlarged vertical sectional view schematically showing a conductive film that covers the silicon wafer.

Next, as shown in FIG. 10, a conductive film 82 is formed on the surface of the silicon wafer 78. The conductive film 82 connects the upper electrodes 25 with respect to each other for each row in each element chip 17. Also, the upper electrode 25 and the upper electrode terminals 34, 36 are formed from the conductive film 82 by a photolithographic technique.

Figure 11:
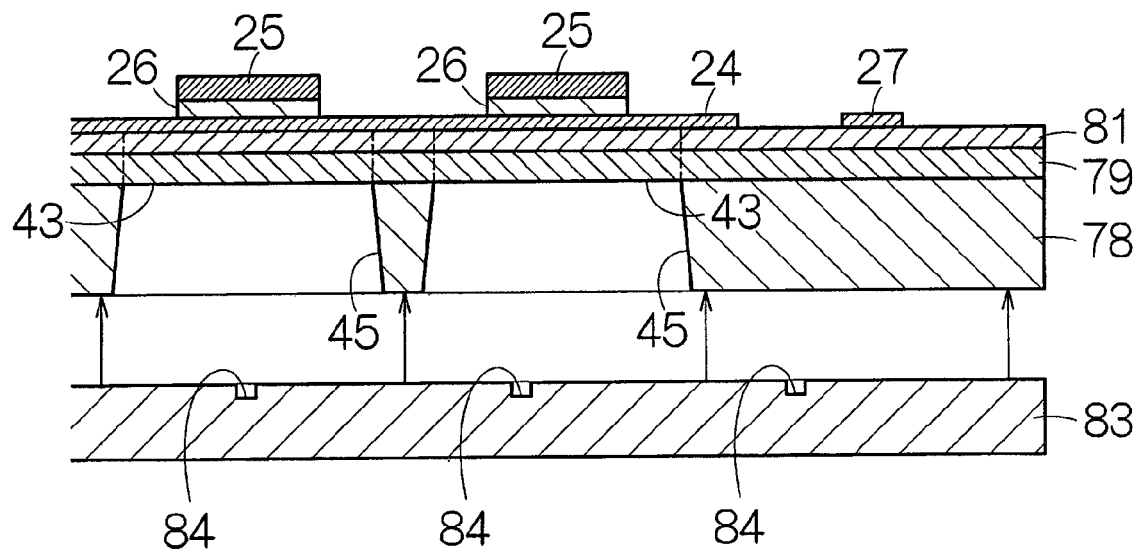
FIG. 11 is a partial enlarged vertical sectional view schematically showing an opening formed in the silicon wafer, and a reinforcing plate wafer.

Next, as shown in FIG. 11, the openings 45 of an array pattern are formed from the reverse surface of the silicon wafer 78. For forming the openings 45, an etching treatment is conducted. The silicon oxide film 79 serves as an etching stop layer. The vibrating film 43 is divided into the silicon oxide film 79 and the zirconium oxide film 81. After the openings 45 are formed, a surface of a reinforcing plate wafer 83 (reinforcing member) is superimposed on the reverse surface of the silicon wafer 78. Before superimposing, the wafer 83 is held on a handling mechanism or a stage. For example, a rigid insulating substrate can be used for the wafer 83. A silicon wafer can be used for the insulating substrate. An adhesive can be used for bonding, for example. After bonding, each of the element chips 17 is cut out of the silicon wafer 78.

Figure 12:
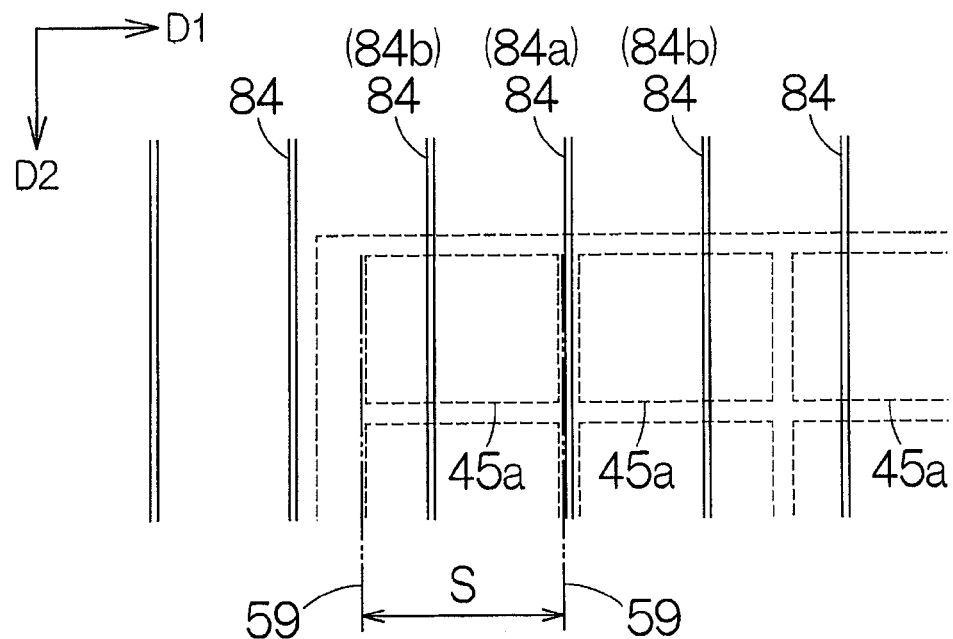
FIG. 12 is a partial enlarged plan view schematically showing the positional relationship of the openings and grooves when the silicon wafer and the reinforcing plate wafer are superimposed.

Before bonding, linear grooves 84 are formed on the surface of the reinforcing plate wafer 83. The grooves 84 extend in parallel to each other at equal intervals. At least one end of the grooves 84 is open at the end surface of the wafer 83. The grooves 84 are aligned at intervals L which are smaller than the opening width S of the openings 45. When the interval L of the grooves 84 is set in this way, even when a relative positional displacement occurs between the silicon wafer 78 and the reinforcing plate wafer 83, it is possible for at least one groove 84 to cut across the outlines 45*a* of the openings 45. For example as shown in FIG. 12, even when the groove 84*a* is positioned between the openings 45 with the reinforcing plate wafer 83 displaced in the first direction D1 in relation to the silicon wafer 78, it is possible for at least one groove 84*b* to be arranged at two openings 45. When each of the element chips 17 is cut out from the silicon wafer 78, the grooves 84 provide the grooves 53 of the reinforcing plate 52.

When grooves 84 are formed in this way, even when the silicon wafer 78 and the wafer 83 are superimposed in air or in another gas atmosphere, superimposing can be achieved relatively easily. On the other hand, when the reverse surface of the silicon wafer 78 is superimposed on an even plane, the gas is pushed into each opening 45 interior by the plane of the reinforcing plate wafer. At atmospheric pressure, gas of greater volume than the volume of the space within the opening 45 tries to remain inside the openings 45. When extra gas does not escape from the interval between the silicon wafer 78 and the reinforcing plate wafer at the same time as sealing off of the openings 45, it is not possible to achieve binding together of the silicon wafer 78 and the reinforcing plate wafer.

(5) Ultrasonic Transducer Element Chip of Other Embodiments

Figure 13:
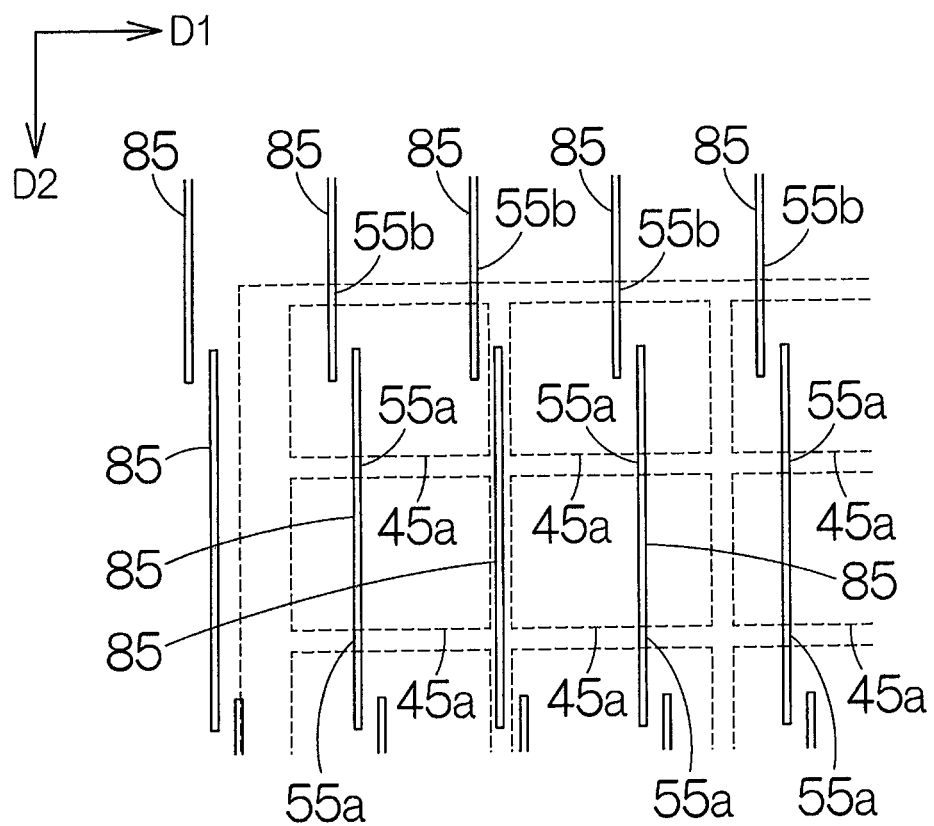
FIG. 13 is a partial enlarged plan view schematically showing the ultrasonic transducer element chip of another embodiment.

FIG. 13 schematically shows the ultrasonic transducer element chip 17*a* of another embodiment. With this element chip 17*a*, each individual groove 85 extends locally in the second direction D2. These local grooves 85 form passages 55*a* and 55*b* between a number of the openings 45. With a combination of a plurality of the grooves 85, in a plan view from the substrate 21 thickness direction, a series of passages 55*a* and 55*b* that cut across one line of openings 45 in sequence and connect openings 45 successively are formed. In this way, it is possible to ensure ventilation for all of one column of openings 45 using a combination of the passages 55*a* and 55*b*. The grooves 85 can be constituted in the same manner as the grooves 53. The remainder of the constitution can be constituted in the same manner as the element chip 17. In the drawing, equivalent constitutions and structures to those of the element chip 17 are given the same reference code numbers.

Figure 14:
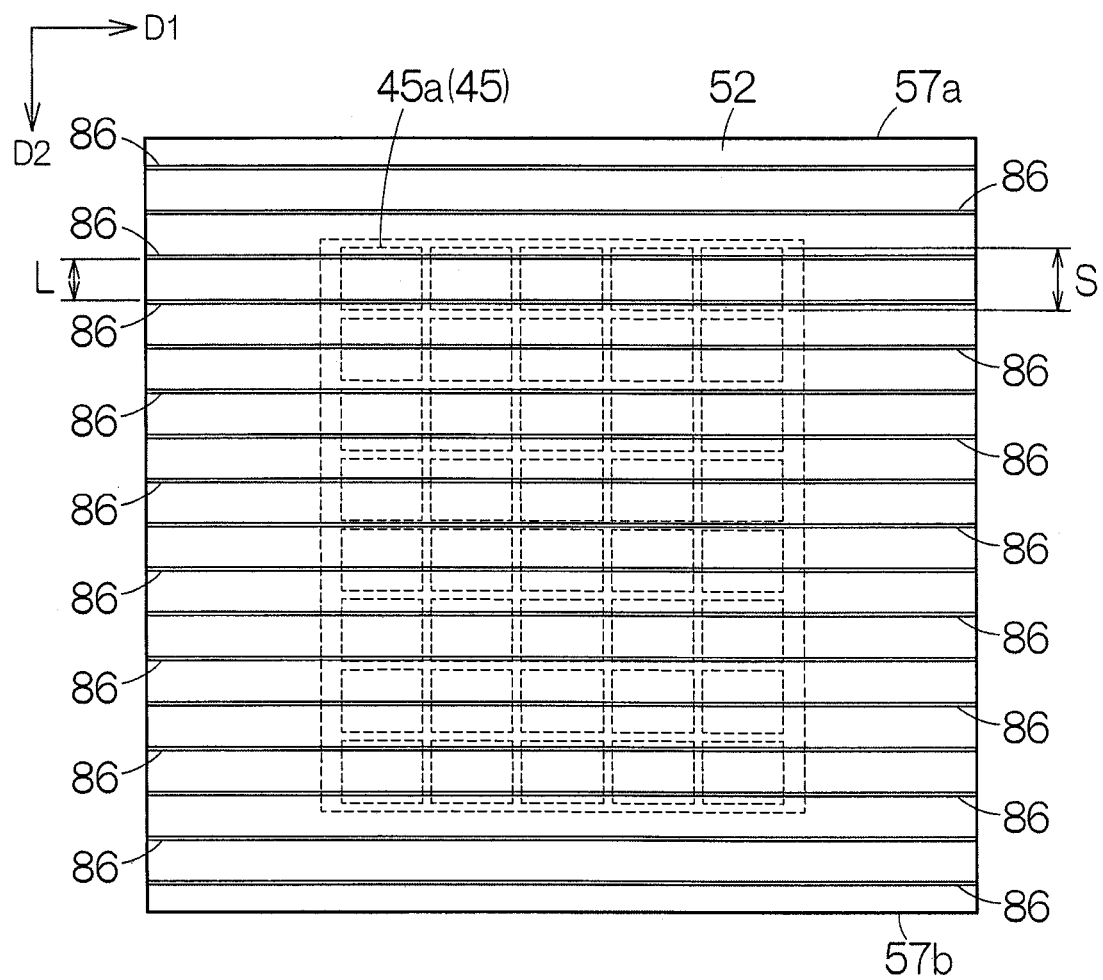
FIG. 14 is a partial enlarged view schematically showing the ultrasonic transducer element chip of yet another embodiment.

FIG. 14 schematically shows the ultrasonic transducer element chip 17*b* of yet another embodiment. With this element chip 17*b*, the grooves 86 extend in the first direction DE specifically, the long side direction of the rectangle. Therefore, in a plan view from the substrate 21 thickness direction, the grooves 86 cut across the outlines 45*a* of the openings 45 at the short side of the rectangle. At the short side of the rectangle, due to the section modulus, the wall of the outline 45*a* of the opening 45, specifically the partition wall 51, does not deform easily. Even if the bonding range becomes narrower based on the formation of the grooves 86, it is possible to maintain relatively high rigidity for the partition wall 51. Therefore, it is possible to inhibit vibration (residual vibration) of the partition wall 51. The remainder of the constitution can be constituted in the same manner as the element chip 17. In the drawing, equivalent constitutions and structures to those of the element chip 17 are given the same reference code numbers.

In addition, for any of the embodiments, it is also possible to use a zigzag pattern for the arrangement of the openings 45. With a zigzag pattern, a group of the elements 23 in an even row may be displaced with respect to a group of the elements 23 in an odd row by one-half of the column pitch. In addition, the grooves 53, 85, and 86 can be inclined at a designated incline angle in relation to the first direction D1 and the second direction D2.

While the present embodiment has been explained in detail as above, it will be apparent to those skilled in the art that various modifications can be made herein without substantially departing from the new matters and the effect of the present invention. Therefore, all such modifications are included in the scope of the invention. For example, the terms used in the specification or the drawings at least once together with a different term having a broader or similar meaning can be replaced with the different term in any portion of the specification or the drawings. Also, the configurations and operations of the ultrasonic diagnostic device 11, the ultrasonic probe 13, the probe head 13*b*, the element chips 17, 17*a*, and 17*b*, the element 23 and the like are not limited to the present embodiment, and various modifications are possible.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An ultrasonic transducer element chip comprising:
   a substrate defining a plurality of openings arranged in an array pattern;
   a plurality of ultrasonic transducer elements respectively disposed at the openings on a first surface of the substrate; and
   a reinforcing member fixed on a second surface of the substrate opposite to the first surface of the substrate to reinforce the substrate, the reinforcing member including a plurality of linear groove parts formed on a surface of the reinforcing member fixed on the second surface of the substrate so that internal spaces of the openings and an external space of the substrate are in communication with each other via the linear groove parts, the linear groove parts extending along a plane of the surface of the reinforcing member, and the linear groove parts being arranged at an interval in a first direction smaller than a width of each of the openings on the second surface of the substrate in the first direction.

2. The ultrasonic transducer element chip according to claim 1, wherein
   the reinforcing member is bonded to a partition wall section of the substrate between the openings in at least one bonding region.

3. The ultrasonic transducer element chip according to claim 1, wherein
   in a plan view seen along a substrate thickness direction, each of the linear groove parts continuously extends across each of a plurality of the openings in a corresponding one of a plurality of columns of the array pattern so that the internal spaces of adjacent ones of the openings in the corresponding one of the columns of the array pattern are in communication with each other and the internal space of one of the openings disposed at an end of the corresponding one of the columns is in communication with the external space disposed outside of an outline of the substrate.

4. The ultrasonic transducer element chip according to claim 1, wherein
   in a plan view seen along a substrate thickness direction, a combination of a plurality of the linear groove parts extends across each of a plurality of the openings in a corresponding one of a plurality of columns of the array pattern so that the internal spaces of adjacent ones of the openings in the corresponding one of the columns of the array pattern are in communication with each other and the internal space of one of the openings disposed at an end of the corresponding one of the columns is in communication with the external space disposed outside of an outline of the substrate.

5. The ultrasonic transducer element chip according to claim 1, wherein
   the interval in the first direction at which the linear groove parts are arranged is ⅓ or greater than and smaller than ½ of the width of each the openings in the first direction.

6. The ultrasonic transducer element chip according to claim 1, wherein
   in a plan view seen along a substrate thickness direction, the openings have rectangular outlines, and the linear groove parts extend across the openings along a short side direction of the rectangle outlines.

7. The ultrasonic transducer element chip according to claim 1, wherein
   in a plan view seen along a substrate thickness direction, the openings have rectangular outlines, and the linear groove parts extend across the openings along a long side direction of the rectangle outlines.

8. The ultrasonic transducer element chip according to claim 1, wherein
   in a plan view seen along a substrate thickness direction, the openings are arranged at a constant pitch in the first direction, and the linear groove parts are arranged at a regular pitch in the first direction.

9. A probe comprising:
   the ultrasonic transducer element chip according to claim 1; and
   a case member supporting the ultrasonic transducer element chip.

10. An electronic instrument comprising:
    the probe according to claim 9; and
    a processing circuit connected to the probe, and configured to process output signals of the ultrasonic transducer elements.

11. An ultrasonic diagnostic device comprising:
    the probe according to claim 9;
    a processing circuit connected to the probe, and configured to process output signals of the ultrasonic transducer elements to generate an image; and
    a display device configured to display the image.

12. A probe head comprising:
    the ultrasonic transducer element chip according to claim 1; and
    a case member supporting the ultrasonic transducer element chip, and configured to be coupled to a probe main body of a probe.

13. A method for manufacturing an ultrasonic transducer element chip comprising:
    holding a reinforcing member including a plurality of linear groove parts formed on a surface of the reinforcing member and arranged at an interval in a first direction smaller than a width of each of a plurality of openings in the first direction, the openings being arranged in an array pattern on a substrate; and
    superimposing the surface of the reinforcing member and a second surface of the substrate opposite to a first surface of the substrate on which a plurality of ultrasonic transducer elements are respectively disposed at the openings.

* * * * *